(12) United States Patent
Pomytkin et al.

(10) Patent No.: US 7,666,908 B2
(45) Date of Patent: Feb. 23, 2010

(54) METHOD FOR ENHANCING COGNITIVE FUNCTION

(76) Inventors: Igor Anatolievich Pomytkin, ul. Malaya Gruzinskaya, bldg. 29. appart. 153, Moscow, 123557 (RU); Pavel Vasilievich Verteletsky, ul. Pogodinskaya, bldg. 2/3, appart. 80, Moscow, 119121 (RU)

( * ) Notice: Subject to any disclaimer, the term of this patent is extended or adjusted under 35 U.S.C. 154(b) by 779 days.

(21) Appl. No.: 11/338,169

(22) Filed: Jan. 24, 2006

(65) Prior Publication Data
US 2006/0199862 A1 Sep. 7, 2006

(30) Foreign Application Priority Data
Mar. 4, 2005 (RU) .............................. 2005106089

(51) Int. Cl.
*A01N 37/00* (2006.01)
(52) U.S. Cl. ...................................... 514/553; 514/574
(58) Field of Classification Search ................. 514/553, 514/574
See application file for complete search history.

(56) References Cited
U.S. PATENT DOCUMENTS
2006/0205815 A1* 9/2006 Patel ........................... 514/552

OTHER PUBLICATIONS
Mark A. McDaniel, "Brain Specific" Nutrients: A Memory Cure?, Psychological Science in the Public Interest, May 1, 2002, p. 12-38, vol. 3.
* cited by examiner

*Primary Examiner*—Sreeni Padmanabhan
*Assistant Examiner*—Renee Claytor
(74) *Attorney, Agent, or Firm*—Notaro & Michalos P.C.

(57) ABSTRACT

The present invention relates to method for enhancing cognitive function in a mammal, comprising administering to a mammal in need thereof an effective amount of a compound of the formula (I):

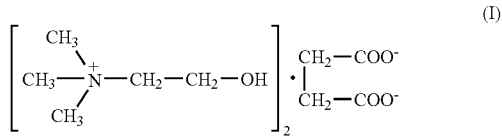

Further, the present invention provides a method for treating a disorder of cognitive function in a mammal, comprising administering to a mammal in need thereof an effective amount of a compound of the formula (I):

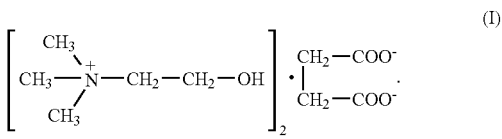

4 Claims, No Drawings

METHOD FOR ENHANCING COGNITIVE FUNCTION

FIELD OF THE INVENTION

The present invention relates to the healthcare, particularly to the enhancement of cognitive function in mammals in need thereof, preferably in humans.

BACKGROUND OF THE INVENTION

Cognition can be described as a mental process that includes the ability to memory, attention, learning, perception, action, problem solving and mental imagery.

Cognitive dysfunctions such as age-associated impairment of mental processes, memory impairments, and dementias are becoming increasingly prevalent in ageing populations. Alzheimer's disease is the most common form of dementia in the elderly. Prevalence studies suggest that in 2000 the number of persons with Alzheimer's disease in the United States was 4.5 million. Without advances in therapy, the number of symptomatic cases in the United States is predicted to rise to 13.2 million by 2050. Hebert L E et al., *Arch Neurol* 2003; 60:1119-1122. Non-Alzheimer's types of dementia include cognitive declines arising from metabolic disorders, toxic injury, hypoxic injury, structural disorders, and infectious diseases. *The Merck Manual of Diagnosis and Therapy. Sect. 14 Neurologic Disorders Chapt.* 171. In other mammals such as dogs, age-associated cognitive dysfunction known as cognitive dysfunction syndrome are frequently observed. Symptoms of cognitive dysfunction syndrome in dogs include memory loss, altered interaction with family members, and decreased activity level Thus, there is a great need in effective and safe agents for enhancing cognitive functions in mammals, especially in humans.

It is known that choline is essential nutrient. It is known that some of choline derivatives have been extensively tested for its effectiveness in treating cognitive disorders and Alzheimer's disease. It has been shown that esters of choline such as phosphatidylcholine and citicoline are useful for improving memory in older adults, whereas the use of dietary choline salts had not the benefits for improving memory. McDaniel M A et al., *Physiological Science in the Public Interest.* 2002, 3(2): 12-38.

A choline salt of succinic acid (chemical name bis[2-hydroxyethyl-N,N,N-trimethylaminium]butanedioate; formula $[(CH_3)_3NCH_2CH_2OH]_2 \cdot OOCCH_2CH_2COO$; and CAS-RN 109438-15-5) has never been tested earlier for its efficacy in enhancing a cognitive function or treating disorders of cognitive function in a mammal.

We found that mentioned above choline salt of succinic acid is much more effective in enhancing cognitive functions than commonly used choline salts such as choline chloride.

It is an object of the present invention to provide the method for enhancing cognitive function in a mammal, comprising administering to a mammal in need thereof an effective amount of the choline salt of succinic acid mentioned above.

It is an object of the present invention to provide the method for treating a disorder of cognitive function in a mammal, comprising administering to a mammal in need thereof an effective amount of the choline salt of succinic acid mentioned above.

SUMMARY OF THE INVENTION

The present invention provides a method for enhancing cognitive function in a mammal, comprising administering to a mammal in need thereof an effective amount of a compound of the formula (I):

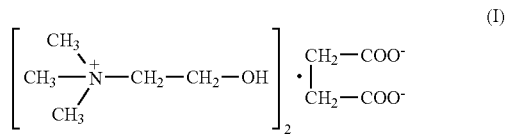

Further, the present invention provides a method for treating a disorder of cognitive function in a mammal, comprising administering to a mammal in need thereof an effective amount of a compound of the formula (I):

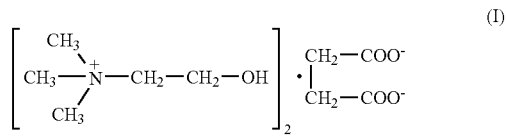

DETAILED DESCRIPTION OF THE INVENTION

The present invention provides a method for enhancing cognitive function in a mammal, comprising administering to a mammal in need thereof an effective amount of a compound of the formula (I):

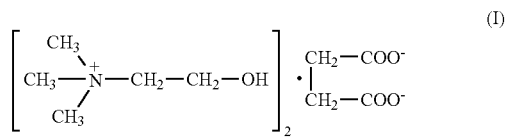

As used herein, the term "enhancing cognitive function" means improving the ability of a mammal to memory, attention, learning, perception, action, planning, problem solving and mental imagery.

In the method of the invention, the enhancing cognitive function can be achieved in healthy mammals as like as in mammals suffering from cognitive dysfunctions. Further, the present invention provides a method for treating a disorder of cognitive function in a mammal, comprising administering to a mammal in need thereof an effective amount of a compound of the formula (I):

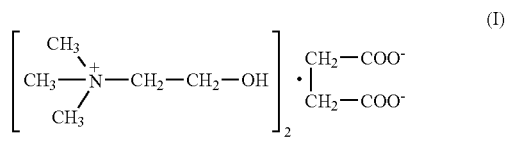

As used herein, the term "treating a disorder of cognitive function" means treating, controlling, preventing and/or reducing one or more clinical signs (i.e., symptoms) of cognitive impairment in a mammal in need thereof. These impairments can result from disorders such as age-associated memory dysfunction, memory loss, mild cognitive impairment, cognitive dysfunction syndrome, and dementias. Such dementias include, but are not limited to, Alzheimer's disease, Lewy body dementia, vascular dementia, dementia caused by chronic cerebral ischemia, AIDS dementia, dementia caused by Parkinson's disease, dementia caused by amyotrophic lateral sclerosis, dementia caused by brain trauma, dementia caused by Huntigton's disease, dementia caused by multiple sclerosis, dementia caused by Pick's disease, dementia caused by vascular disease, dementia caused by organ system failure, dementia caused by metabolic diseases, and dementia caused by infectious. Generally recognized compendiums of disorders that accompanied with decline of cognitive functions are *Merck Manual of Diagnosis and Therapy*. Sect. 14 *Neurologic Disorders, Chapt*. 171. *Merck Manual of Geriatrics Sect*.5, Chapt. 40.

In methods of the invention, the compound of the formula (I) is administered orally or parenterally for 1 day or longer in a variety of dosage forms. Such dosage forms include, but are not limited to, tablets, capsules, powders, solutions, water solutions, aerosols, elixirs, syrups, and injections.

In methods of the invention, the compound of the formula (I) can be used as drug or a medical food for enhancing cognitive function or treating a disorder of cognitive function.

Preferably, the effective amount of the compound of the formula (I) is 0.1 to 50 mg per kilogram of body weight of the mammal.

Nonexclusive examples of mammals of the invention include humans and companion animals such as cats and dogs. Preferably, the mammal is a human.

Because of enhancing cognitive function or treating a disorder of cognitive function, it is now possible to improve life quality in persons suffering from age-associated decline in cognitive functions.

The following examples are presented to demonstrate the invention. The examples are illustrative only and are not intended to limit the scope of the invention in any way.

EXAMPLE 1

The example shows that administering an effective amount of a compound of the formula (I) enhanced cognitive function in rats with cognitive impairments induced by chronic cerebral ischemia.

The effect of the compound of the formula (I) on cognitive function was assessed in rats with chronic cerebral ischemia induced by chronic bilateral ligation of common carotid arteries. The ligation was made in Wistar male rats 3 hours prior the first injection of the compound of the formula (I) or saline. Rats were injected i.p. with 1 mg/kg or 50 mg/kg the compound of the formula (I) or saline (control) for 7 days singly a day. Passive avoidance step-through paradigm test (short-term learning) was made on day $8^{th}$ since the ligation. The pre-shock and post-shock latency time was used as an index of cognitive impairments. The latency time in group of shame-operated rats was 9.3±2.5 s before the shock and 104.2±22.9 s 24 hours after the shock. Data are presented in table 1 as the latency time mean±SD (n=8).

TABLE 1

| Treatment | Latency, s | |
|---|---|---|
| | Pre-shock | Post-shock |
| Control (saline) | 29.0 ± 10.9 | 30.7 ± 13.1 |
| Compound of the formula (I), 1 mg/kg | 13.5 ± 4.3 | 99.3 ± 24.5* |
| Compound of the formula (I), 50 mg/kg | 27.7 ± 13.1 | 53.3 ± 16.3* |

*Denotes statistically significant difference of control ($p < 0.05$).

Thus, administering the compound of the formula (I) significantly enhanced cognitive function under condition of cognitive impairments induced by chronic cerebral ischemia as compared to the control.

EXAMPLE 2

The example shows that administering an effective amount of a compound of the formula (I) enhanced cognitive function in rats with cognitive impairments induced by amyloid injection.

Beta-amyloid 25-35 (A-beta 25-35) was injected in nucleus basalis magnocellularis (NBM) of rats to induce model of cognitive impairments relevant to human Alzheimer's disease as described. Harkany T et al., *Behav Brain Res*. 1998 90(2):133-45. Harkany T et al., *Prog Neuropsychopharmacol Biol Psychiatry*. 1999 23(6):963-1008.

A-beta 25-35 was administered bilaterally into NBM of male Wistar rats in dose of 2 μg per each side. Since $16^{th}$ day of A-beta 25-35 injection, rats were injected i.p. with 1 mg/kg or 50 mg/kg the compound of the formula (I) or saline (control) for 7 days singly a day. The effect of the compound of the formula (I) on cognitive functions was tested in a model of spontaneous alteration in Y-maze at next day from the day of the last injection. It is a suitable model for assessing memory impairments. Total number of visited arms and number of repeated visits to the same arm for 5 min was counted. In the group of practically healthy shame-operated rats (without injection of A-beta 25-35), the total number of visited arms was 2.71±0.29 and the number of repeated visits was 0.29±0.18. Data are presented in table 2 as the number of visits mean±SD (n=8).

TABLE 2

| Treatment | Number of visits | |
|---|---|---|
| | Total | Repeated |
| Control (saline) | 1.67 ± 0.23 | 1.50 ± 0.50 |
| Compound of the formula (I), 1 mg/kg | 3.00 ± 0.41* | 0.65 ± 0.24* |
| Compound of the formula (I), 50 mg/kg | 2.55 ± 0.33* | 0.75 ± 0.29* |

*Denotes statistically significant difference of control ($p < 0.05$).

Thus, the amyloid toxicity significantly impaired cognitive function (working memory) as compared to shame-operated rats. Treating with the compound of the formula (I) significantly enhanced cognitive function (memory) impaired by amyloid toxicity as compared to the control.

We claim:

1. A method for enhancing cognitive function in a mammal, comprising administering to a mammal in need thereof an effective amount of a compound of the formula (I):

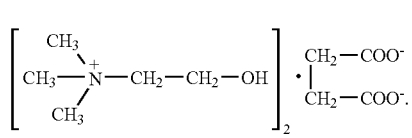

(I)

2. The method as claimed in claim 1 wherein the effective amount of the compound of the formula (I) is 0.1 to 50 mg per kilogram of body weight of the mammal.

3. A method for treating symptoms of cognitive impairment in mammals, comprising administering to a mammal in need thereof an effective amount of a compound of the formula (I):

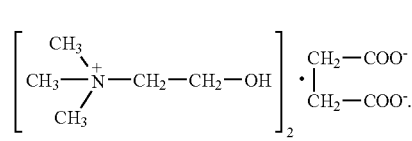

(I)

4. The method as claimed in claim 3 wherein the effective amount of the compound of the formula (I) is 0.1 to 50 mg per kilogram of body weight of the mammal.

* * * * *